(12) United States Patent
Flegel

(10) Patent No.: US 8,723,361 B2
(45) Date of Patent: May 13, 2014

(54) AUTOMATIC TRANSFER SWITCH HAVING AN INTERLOCK ARRANGEMENT

(71) Applicant: Reliance Controls Corporation, Racine, WI (US)

(72) Inventor: David D. Flegel, Racine, WI (US)

(73) Assignee: Reliance Controls Corporation, Racine, WI (US)

( * ) Notice: Subject to any disclaimer, the term of this patent is extended or adjusted under 35 U.S.C. 154(b) by 24 days.

(21) Appl. No.: 13/755,430

(22) Filed: Jan. 31, 2013

(65) Prior Publication Data

US 2013/0140904 A1 Jun. 6, 2013

Related U.S. Application Data

(63) Continuation of application No. 12/396,815, filed on Mar. 3, 2009, now Pat. No. 8,471,659.

(60) Provisional application No. 61/033,810, filed on Mar. 5, 2008.

(51) Int. Cl.
*H02J 7/00* (2006.01)
*H02J 9/00* (2006.01)

(52) U.S. Cl.
CPC ..... *H02J 7/00* (2013.01); *H02J 9/00* (2013.01)
USPC .............................. 307/64; 307/23; 307/126

(58) Field of Classification Search
CPC ...................................... H02J 7/00; H01J 9/00
USPC .................. 335/6, 13, 61, 106, 64–68, 85–87
See application file for complete search history.

(56) References Cited

U.S. PATENT DOCUMENTS

| | | | |
|---|---|---|---|
| 3,736,054 A | 5/1973 | Loffler et al. | |
| 3,778,633 A | 12/1973 | DeVisser et al. | |
| 4,157,461 A | 6/1979 | Wiktor | |
| 4,398,097 A | 8/1983 | Schell et al. | |
| 4,423,336 A | 12/1983 | Iverson et al. | |
| 4,760,278 A | 7/1988 | Thomson | |
| 5,023,469 A | 6/1991 | Bassett et al. | |
| 5,397,868 A | 3/1995 | Smith et al. | |
| 5,745,670 A | 4/1998 | Linde | |
| 5,831,345 A | 11/1998 | Michaud | |
| 5,914,467 A | 6/1999 | Jonas et al. | |
| 6,100,604 A | 8/2000 | Morroni et al. | |
| 6,169,340 B1 | 1/2001 | Jones | |
| 6,172,432 B1 | 1/2001 | Schnackenberg et al. | |
| 6,181,028 B1 | 1/2001 | Kern et al. | |
| 2006/0221533 A1 * | 10/2006 | Lathrop et al. | 361/160 |

OTHER PUBLICATIONS

"GenReady Load Center and Transfer Switch" Sell Sheet; Generac Power Systems, Inc., P.O. Box 8, Waukesha, WI 53187, 2008, 6 pages.
"Installation Instructions GenReady Load Center EZ Transfer Operator, Model #005447-0", Revisions C, Mar. 4, 2008, Generac Power Systems, Inc., 8 pages.

* cited by examiner

*Primary Examiner* — Rexford Barnie
*Assistant Examiner* — Toan Vu
(74) *Attorney, Agent, or Firm* — Ryan Kromholz & Manion, S.C.

(57) ABSTRACT

An automatic transfer switch to automatically electrically connect an electrical panel to a second power source, e.g., an electric generator, during interruption or failure of a first power source, e.g., a utility power supply, includes a powered interlock arrangement that is operative to prevent the electrical panel from being electrically connected to both power sources simultaneously.

7 Claims, 9 Drawing Sheets ized solenoid may only be energized for a period sufficient to retract its carriage. In this regard, neither solenoid maintains a holding force on its carriage after the carriage has been retracted.

AUTOMATIC TRANSFER SWITCH HAVING AN INTERLOCK ARRANGEMENT

RELATED APPLICATIONS

This is a continuation application of U.S. patent application Ser. No. 12/396,815, filed Mar. 3, 2009, which claims the benefit of U.S. Provisional Patent Application Ser. No. 61/033,810, filed Mar. 5, 2008, and entitled "Automatic Transfer Switch Having An Interlock Arrangement," which is incorporated herein by reference.

FIELD OF THE INVENTION

The present invention relates generally to power management systems designed to energize the distribution circuits of an electrical panel using an auxiliary or backup power source during primary power interruption. More particularly, the invention is directed to an automatic transfer switch having interlinked switch members to prevent two power sources from feeding power to the electrical panel simultaneously.

BACKGROUND OF THE INVENTION

Manual transfer switches are sufficient for most applications where, during a utility power outage, a homeowner, landlord, or property manager is available to startup a generator, make the necessary temporary electrical interconnections, and operate the transfer mechanism. This type of system is popular in part because of its simplicity and the modest equipment and installation costs involved.

However, such a manually actuated transfer system may not be suitable in some cases, particularly when no one is in attendance or where more convenience is desired or required. In such cases, a fully automatic transfer switch, operating in conjunction with a permanently installed alternate power source (such as a generator) might be preferred. The need for an electrical transfer device to safely switch between utility and generator power is well documented.

U.S. Pat. No. 6,031,193, the entire disclosure of which is incorporated herein by reference, describes an interlock arrangement for interlinking circuit breakers. This patent describes an interlock structure that causes the handle of a circuit breaker to first move a switch to an OFF position in response to an operator pushing the handle of an opposite circuit breaker to an ON position. In this regard, both circuit breakers cannot simultaneously be in the ON position. The result is that power cannot be supplied to a panel bus from two sources at one time, and one source cannot back-feed the other. Heretofore, such interlock structures have been limited to manual transfer switches.

SUMMARY OF THE INVENTION

The present invention is directed to an actuating arrangement, such as may be used in connection with an automatic transfer switch that incorporates interlinked switches. In operation, when the loss or interruption of primary power is sensed, an auxiliary power supply, such as an electric generator, is energized, and then a powered actuator is activated to cause a switching member to translate linearly relative to the switch handles of a pair of aligned interlinked switches. The switching member is constructed such that the translation imparted by the actuator first causes a switch member to be moved to the OFF position so as to electrically isolate the electrical panel from a first power supply, e.g., a utility power grid, and then causes a second switch member to be moved to the ON position so as to electrically connect the electrical panel to a second power supply, e.g., an electric generator.

In one preferred implementation, the present invention is used with an automatic transfer switch that automatically electrically connects one or more distribution circuits to an auxiliary power supply, e.g., an electric generator, when a primary power supply, e.g., a utility power grid, fails to supply power to the distribution circuits. When the primary power is interrupted, this loss of power is sensed by the auxiliary power supply, which in turn provides a signal to the automatic transfer switch to switch the auxiliary feeder switch from an OFF position to an ON position so that the distribution circuits are connected to be fed power from the auxiliary power supply instead of the primary power supply. The present invention, however, provides the additional functionality of electrically isolating the distribution circuits from the primary power supply by switching a primary feeder switch from the ON position to the OFF position. Thus, the present invention prevents the distribution circuits from being fed primary power when the primary power is restored. Moreover, the present invention provides an interlinking between the feeder switches such that the primary feeder switch is switched OFF before the auxiliary feeder switch is switched ON.

When primary power is restored, the auxiliary feeder switch is automatically and firstly switched from the ON position to the OFF position and then the primary feeder switch is automatically switched from the OFF position to the ON position. The interlinking between the feeder switches causes the switches to be switched in tandem thereby preventing the primary power supply from feeding power to the distribution circuits when the auxiliary power supply is feeding power to the distribution circuits.

The actuating arrangement may include a pair of opposed actuators, such as solenoids, connected to respective carriages that are in turn connected to respective levers that are positioned generally adjacent respective breakers or switch members and that are configured to pivot about a pivot axis. One solenoid is energized when the primary power is restored and the other solenoid is energized when the auxiliary or auxiliary power supply is started up. In this embodiment, when a solenoid is energized, it applies a pulling force to its carriage, which in turn causes its lever to pivot so that lever pushes the switch member associated therewith from an ON position to an OFF position. An interlinking member associated with the switch member causes the other switch member to be pulled from its OFF position to its ON position; however, the other switch member is not placed in the ON position until the other switch member is in the OFF position. An energized solenoid may only be energized for a period sufficient to retract its carriage. In this regard, neither solenoid maintains a holding force on its carriage after the carriage has been retracted.

In accordance with one aspect, the present invention provides a transfer panel including a plurality of circuit breakers for controlling current flow to a plurality of distribution circuits. The transfer panel has a first and a second switch respectively having first and second switch members oriented such that the switch members are disposed away from each other when the switch members are in the OFF position and towards each other when the switch members are in the ON position. An interlock mechanically interlinks the first and second switch members such that the first and second switch members are switched in tandem. A powered actuator arrangement is configured to apply an actuating force to at least one of the first and second switch members to move the first and second switch members from a first position to a second position.

The powered actuator arrangement may include an electromechanical actuator arrangement that includes first and second opposed solenoids associated with the first and second switch members, respectively, and first and second carriages associated with the first and second solenoids, respectively. The carriages are designed to transfer a linear force applied thereon by the solenoids to a respective one of the switch members.

The electromechanical actuator arrangement may further include first and second levers associated with the first and second carriages, respectively, and the levers are designed to pivot in response to a linear movement of the carriages. When a solenoid is energized to pull its carriage, the lever associated with that carriage applies a pushing force on the switch member.

The interlock may include a control member that transfers a linear force applied to one of the switch members to the aligned opposite switch member so that the switch members are switched in tandem or during a single switching operation.

In accordance with another aspect, the present invention contemplates an actuator for automatically switching a pair of aligned switches. Each aligned switch has an external switch member and the actuator has a solenoid and a linkage coupled to the solenoid and configured to translate linearly in response to a force applied by the solenoid. A lever is coupled to the linkage and configured to translate a linear force of the solenoid to the pair of aligned switches to move the aligned switches in tandem.

According to another aspect, the invention contemplates a method of switchably and automatically connecting distribution circuits of an electrical panel between first and second power supplies. The method includes detecting interruption of power from a power source providing power to the electrical panel. The method further includes energizing a powered actuator connected to power supply switches of the electrical panel to apply a linear force to at least one of the power supply switches to move the power supply switches from a first position to a second position. When the power supply switches are in the second position, the distribution circuits may be fed power from the second power supply.

In accordance with yet another aspect, the present invention provides a transfer panel for electrically connecting a set of distribution circuits to an auxiliary power supply during interruption of primary power from a primary power supply. The transfer panel has a primary side switch having a primary side switch member switchable between an ON position and an OFF position and an auxiliary side switch having an auxiliary side switch member switchable between an ON position and an OFF position. An interlinking member is connected between the primary side switch member and the auxiliary side switch member such that both switch members cannot be in the ON position at the same time. The transfer panel further includes an actuator arrangement that automatically applies a linear force to move the auxiliary side switch member to the ON position when the primary power supply fails to supply power, and the interlinking member causes the primary side switch member to automatically switch to the OFF position before the auxiliary side switch member is switched to the ON position.

It is therefore an object of the invention to provide an automatic transfer switch having an interlock that prevents multiple power sources from feeding power to the transfer switch simultaneously.

It is another object of the invention to provide an electrical panel outfitted with a transfer switch that automatically connects the electrical panel to a auxiliary primary supply when primary power is interrupted and substantially simultaneously electrically isolates the electrical panel from the primary power supply to prevent the backfeeding of power when the primary power supply is restored.

It is another object of the invention to provide an interlock arrangement for an automatic transfer switch or panel.

Various other features, aspects, objects and advantages of the present invention will be made apparent from the following detailed description and the drawings.

BRIEF DESCRIPTION OF THE DRAWINGS

The drawings illustrate one preferred embodiment presently contemplated for carrying out the invention.

DETAILED DESCRIPTION OF THE INVENTION

Figure 1:
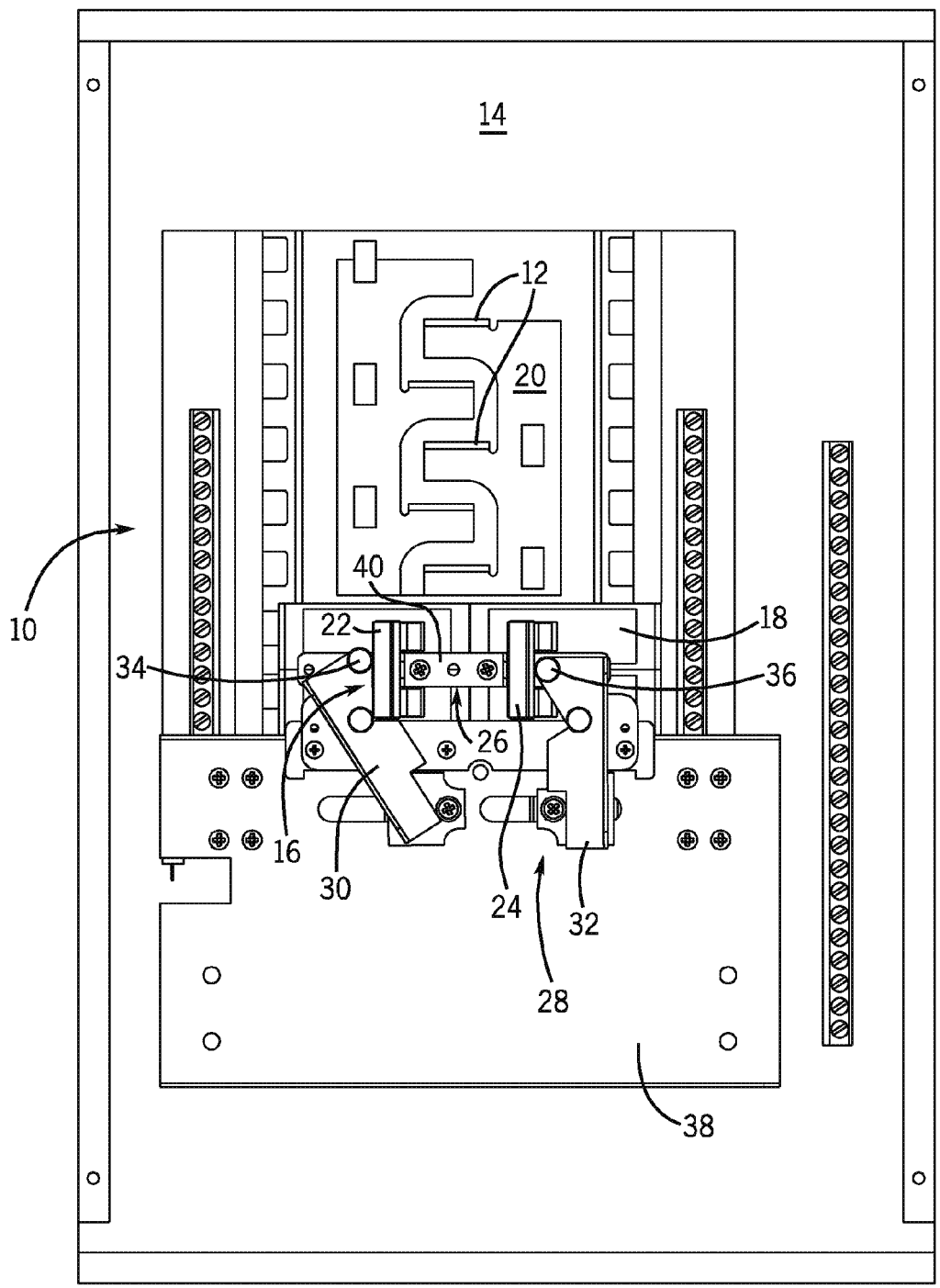
FIG. 1 is a front elevation view of an electrical panel having an automatic transfer switch and an interlock arrangement according to one aspect of the invention.

Referring now to FIG. 1, the present invention is particularly well suited for use with an electrical panel 10 having a series of circuit breakers (not shown) mounted on stabs 12, in a known manner, that control current flow to a number of distribution circuits. The electrical panel 10 is positioned within a cabinet 14 that is mounted or otherwise attached to a wall or similar support structure of a building. In addition to the distribution circuit breakers, the electrical panel 10 also includes a utility side power supply switch, which may be in the form of a breaker 16, and a generator side power supply switch, which may be in the form of a breaker 18. The power supply breakers 16, 18 control which power source energizes a bus bar 20.

Power supply breakers 16, 18 have respective switch handles 22, 24 that are interlinked by an interlock arrangement 26. The switch handles are movable between ON and OFF positions, wherein the ON position for a switch is defined by the switch being moved toward the other switch handle and the OFF position is defined by the switch being moved away from the other switch handle. The interlock arrangement 26 prevents both switch handles from being positioned toward one another at the same time, e.g., both in the ON position, but does allow both switch handles to be moved away from one another at the same time, e.g., both in the OFF position. An exemplary interlock arrangement is shown and described in U.S. Pat. No. 6,031,193, the entire disclosure of which is incorporated herein by reference. As known in the art, by interlinking the switch handles 22, 24, both power breakers cannot be in the ON position at the same time. As such, the electrical panel can only be fed by one power source at a time.

A linkage arrangement 28 is mounted to the electrical panel 10 proximate to the switch handles 22, 24. The linkage arrangement 28 includes a first lever 30 associated with and designed to operate switch handle 22 and a second lever 32 associated with and designed to operate switch handle 24. As will be described more fully below, lever 30 has a raised boss 34 that pushes against switch handle 22 when the switch handle 22 is being switched from the OFF position to the ON position, as shown in FIG. 1. Similarly, lever 32 has a raised boss 36 that pushes against switch handle 24 when the switch handle 24 is being switched from the OFF position to the ON position. The linkage arrangement 28 is supported by a mounting bracket 38 that is mounted to the electrical panel 10 in a conventional manner.

Figure 2:
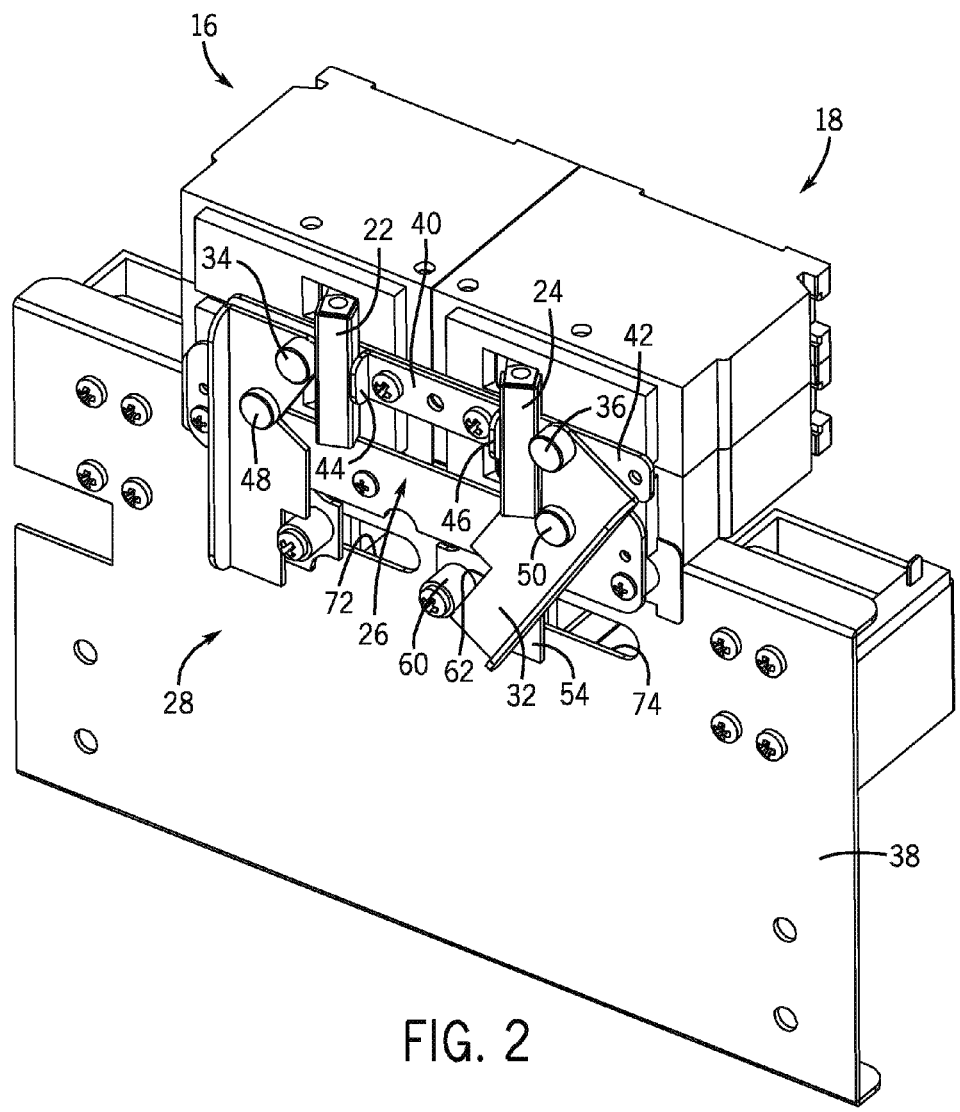
FIG. 2 is a front isometric view of the automatic transfer switch illustrated in FIG. 1 and shown having a utility power supply switch in a ON position and a backup generator power supply switch in an OFF position.

With additional reference to FIG. 2, interlock arrangement 26 includes a control member 40 that is fastened to a bar 42 that is slidable along the faces of the circuit breakers 16, 18. The control member 40 fits in a space (not numbered) defined between the aligned and opposed switch handles 22, 24 and is also slidable with bar 42. The control member 40 has a pair of flanges 44, 46 that engage respective ones of the switch handles 22, 24. The control member 40 is designed such that switch handle cannot be switched to the ON position, such as is shown in connection with switch handle 22 in FIG. 2, without first causing the other switch handle, e.g., switch handle 24, to be moved to the OFF position. Movement of a switch handle from the ON position to the OFF position, such as manually by an operator, does not cause the control member 40 to slide. In this regard, the control member 40 allows for both switch handles 22, 24 to be in the OFF position at the same time, but only one switch handle can be in the ON position at one time. One skilled in the art will appreciate that the control member 40 slides in response to a pushing force applied thereto by a switch handle ("driving switch handle") being switched toward the other switch handle ("driven switch handle"). In this regard, the driving switch handle engages and presses against the flange adjacent thereto, causing the control member 40 to slide as the driving switch handle is moved to the ON position. With the driven switch handle in the ON position, the opposite flange will engage and press against the driven switch handle. As the control member is slid by the driving switch handle, the control member will cause the driven switch handle to move to the OFF position.

Lever 30 pivots about a pivot pin 48 and lever 32 pivots about a pivot pin 50. Each lever pivots about its respective pivot pin either in an active pivoting event or in a passive pivoting event. In an active pivoting event, lever 30 is caused to pivot about pin 48 by retraction of a carriage 52. Similarly, in an active pivoting event lever 32 is caused to pivot about pin 50 by retraction of a carriage 54. Carriage 52 includes a raised boss 56 that engages an edge 58 of the lever 30 during an active pivoting event. Carriage 54 also has a raised boss 60 that engages an edge 62 of lever 32 during an active pivoting event. It will be appreciated that, for a switching event, there can only be one active pivoting event and, if a switch handle is being driven from the ON position to the OFF position, only one passive pivoting event. When one switch handle is being moved from the OFF position to the ON position, this movement is caused by an active pivoting event of the lever associated with that switch handle. The opposite switch handle— the driven switch handle—will cause a pivoting of its lever, which is defined as a passive pivoting event. In other words, during an active pivoting event, the lever will apply a pushing force on its associated switch handle. During a passive pivoting event, the switch handle pushes against the lever causing the lever to pivot about its pivot axis.

Figure 3:
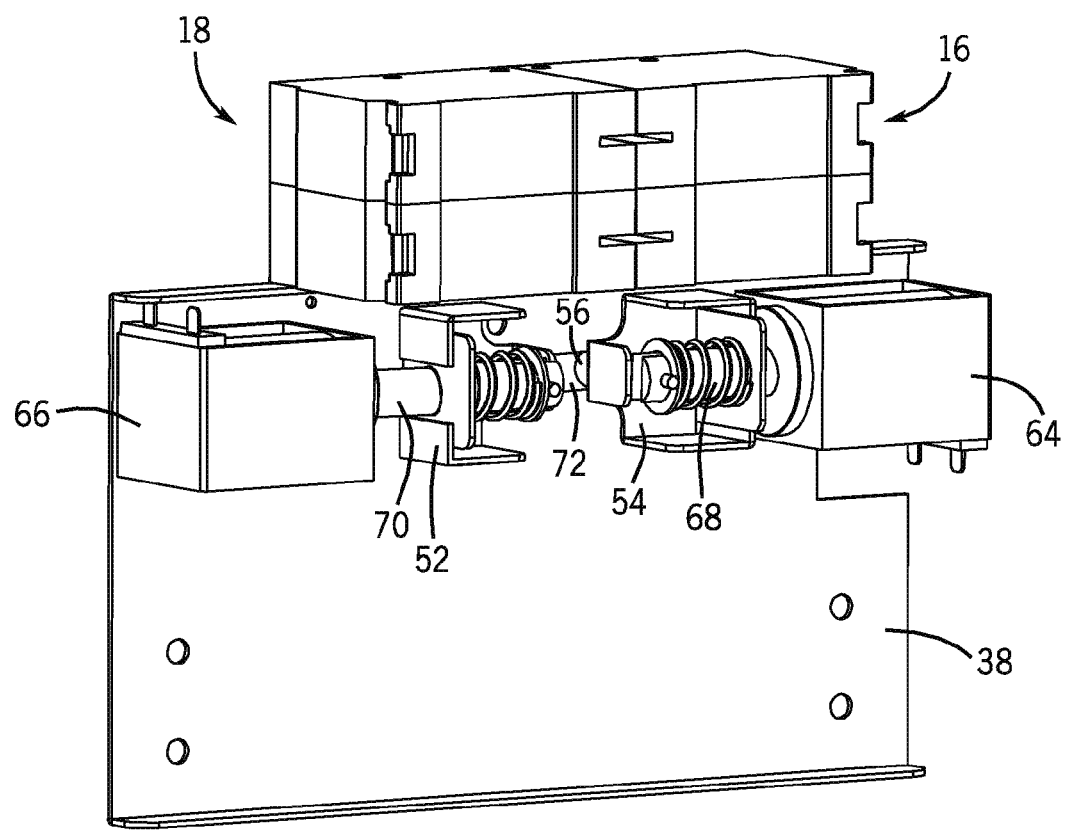
FIG. 3 is a rear isometric view of the automatic transfer switch shown in FIG. 2.

Referring now to FIG. 3, the levers 30, 32 are actively pivoted by respective electromechanical actuators, which in one preferred embodiment are solenoids 64, 66. Solenoid 64 has an armature 68 that is connected to carriage 54. Solenoid 66 likewise has an armature 70 that is connected to carriage 52. As shown in FIG. 2, carriages 52, 54 slide within lateral slots 72, 74, respectively. Linear movement of an armature causes linear movement of the carriage connected thereto in its respective slot, which in turn causes pivoting of the lever associated with the carriage. In a preferred embodiment, the solenoids are pull-type actuators and each thus retracts it is respective armature, and its associated carriage, when energized.

Figure 4:
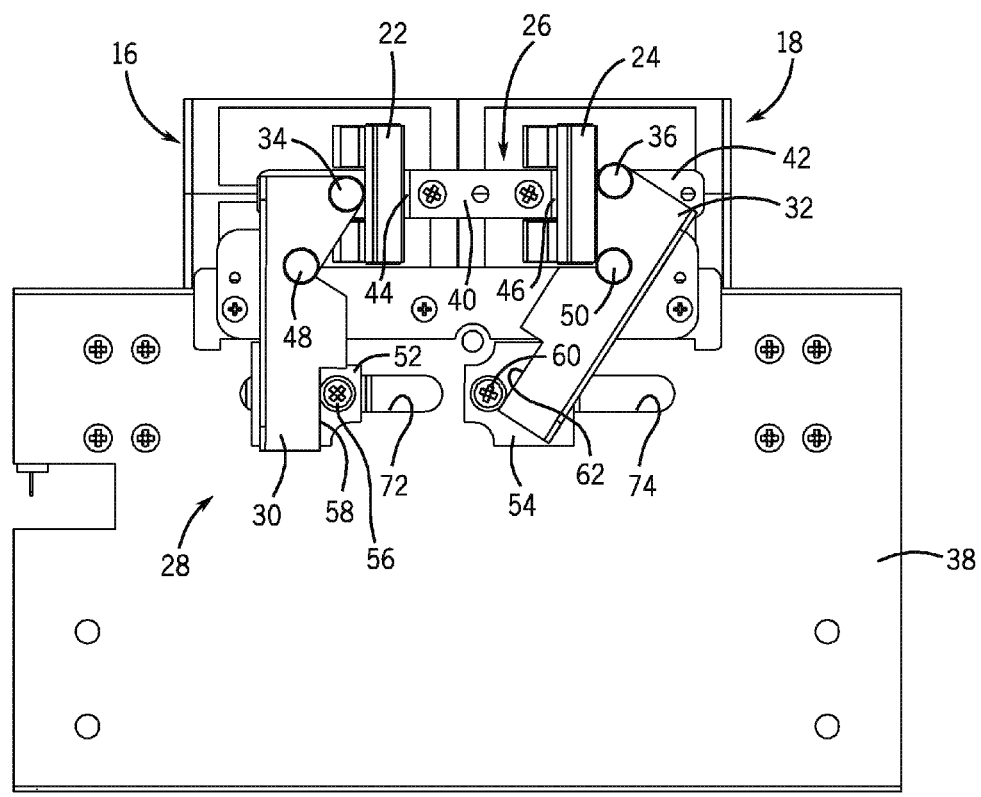
FIG. 4 is a front elevation view of the automatic transfer switch shown in FIG. 2.
Figure 5:
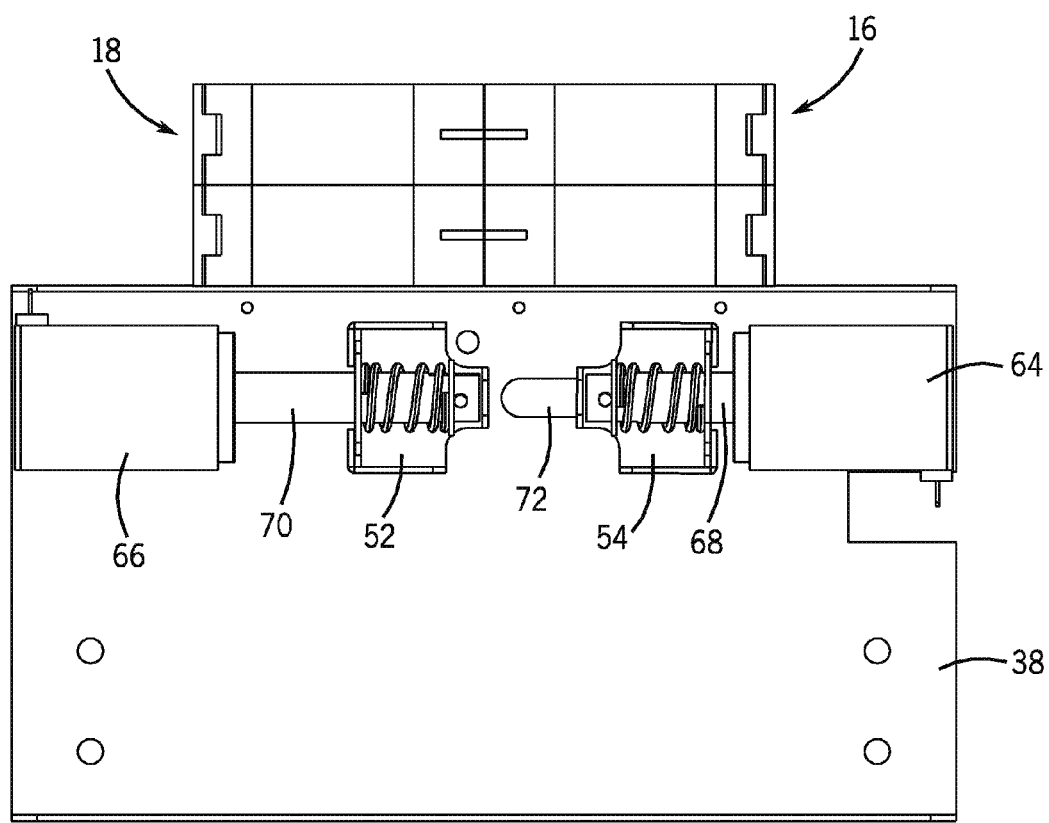
FIG. 5 is a rear elevation view of the automatic transfer switch shown in FIG. 4.
Figure 6:
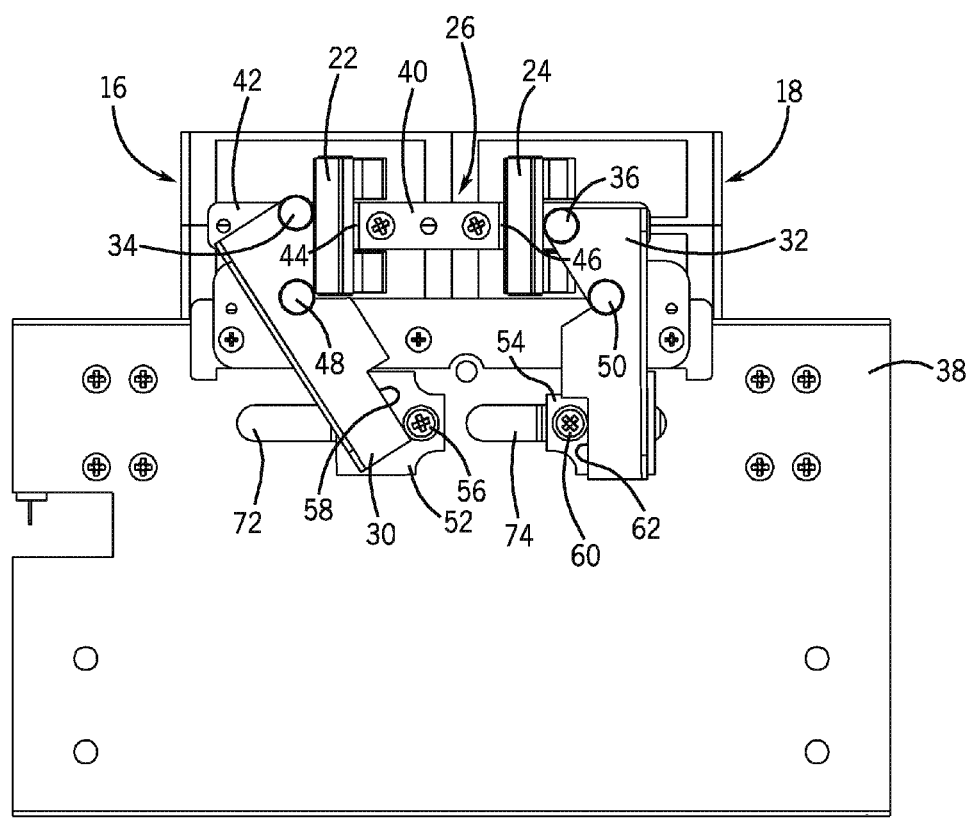
FIG. 6 is a front isometric view of the automatic transfer switch shown in FIG. 1 with the utility power supply switch in an OFF position and the auxiliary power supply switch in the ON position.

Referring now to FIGS. 4-6, when utility power is energizing the electrical panel 10, switch handle 22 will be in the ON position and the switch handle 24 will be in the OFF position, as shown in FIG. 4. Lever 30 will have a generally vertical orientation with carriage 52 positioned generally at a left end of slot 72. Conversely, with switch handle 24 in the OFF position, lever 32 is in a rightward pivoted position with carriage 54 positioned at a generally left end of slot 74. The control member 40 prevents switch handle 24 from being in the ON position when switch handle 22 is in the ON position. It is noted that the mechanics of the circuit breaker 16 holds the switch handle 22 in the ON position and not solenoid 64.

When utility power is interrupted, the generator will be started. After a defined period to allow the generator to reach steady-state operation, the solenoid 66 will be energized under power from the generator, thereby retracting armature 70 and carriage 52 coupled to the armature 70. As the armature 70 retracts, boss 60 extending from carriage 52 will push against edge 62 of lever 32. With continued retraction of armature 70 and movement of carriage 52 rightward in slot 72, the lever 32 will be caused to pivot or rotate in a counter-clockwise direction about pin 50. As the lever 32 rotates, boss 36 applies a linear force to switch handle 24 to move switch handle 24 toward switch handle 22 to the ON position. The switch handle 24 transfers the linear force applied against it to control member 40 which in turn is pushed away from switch handle 24. The control member 22 is engaged with switch handle 22 so that, as the control member slides away from switch handle 24, the control member 40 pushes switch handle 22 away from switch handle 24, e.g., from the ON position to the OFF position. When the switch handle 22 reaches an over-centered position, the mechanics of the circuit breaker 16 causes the switch handle 22 to move to its OFF position before the switch handle 24 reaches its ON position. Thus, the bus bar 20 is electrically isolated from the utility power supply before it is electrically connected to the electric generator. FIG. 6 illustrates the position of the switch handles and the levers when the electrical panel 10 may be fed power from the generator.

In a preferred embodiment, power from the generator is used to power the solenoid 66. Similarly, in a preferred embodiment, utility power is used to power solenoid 64.

When utility power is restored, the solenoid 64 will retract its armature 68, which causes lever 30 to pivot in a clockwise manner about pivot pin 48. As the lever 30 pivots, boss 34 engages switch handle 22 and pushes the switch handle 22 from the OFF position to the ON position. The control member 40 causes the switch handle 24 to first be moved to its OFF position. As such, when utility is restored, the electrical panel 10 is not electrically connected to both the utility power grid and the generator. Thereafter, the generator may be shut-down in a conventional manner.

Figure 7:
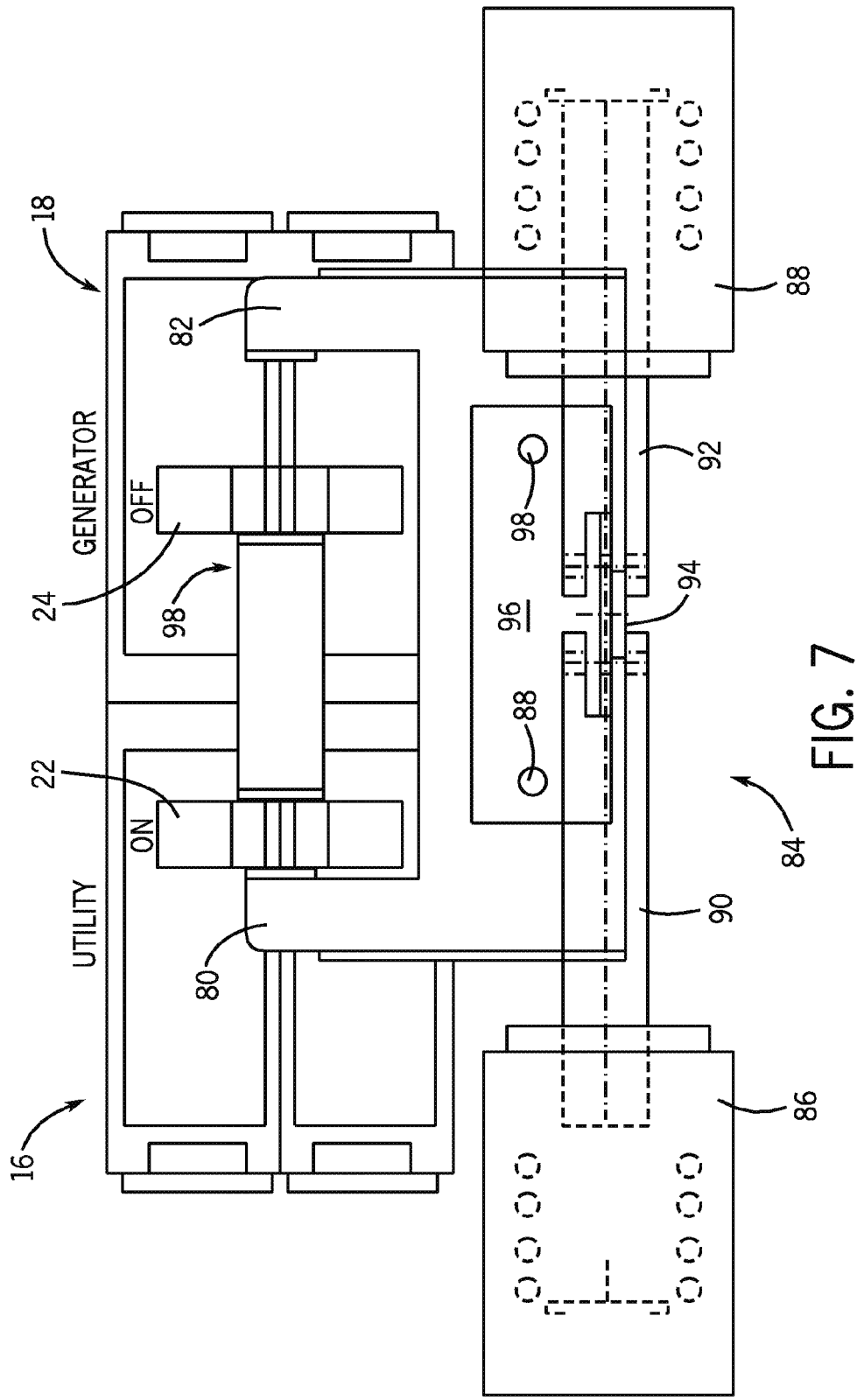
FIG. 7 is a front elevation view of an automatic transfer switch having a shuttle arrangement according to an alternate embodiment of the invention and a utility power supply switch in the ON position and an auxiliary generator power supply switch in the OFF position.
Figure 8:
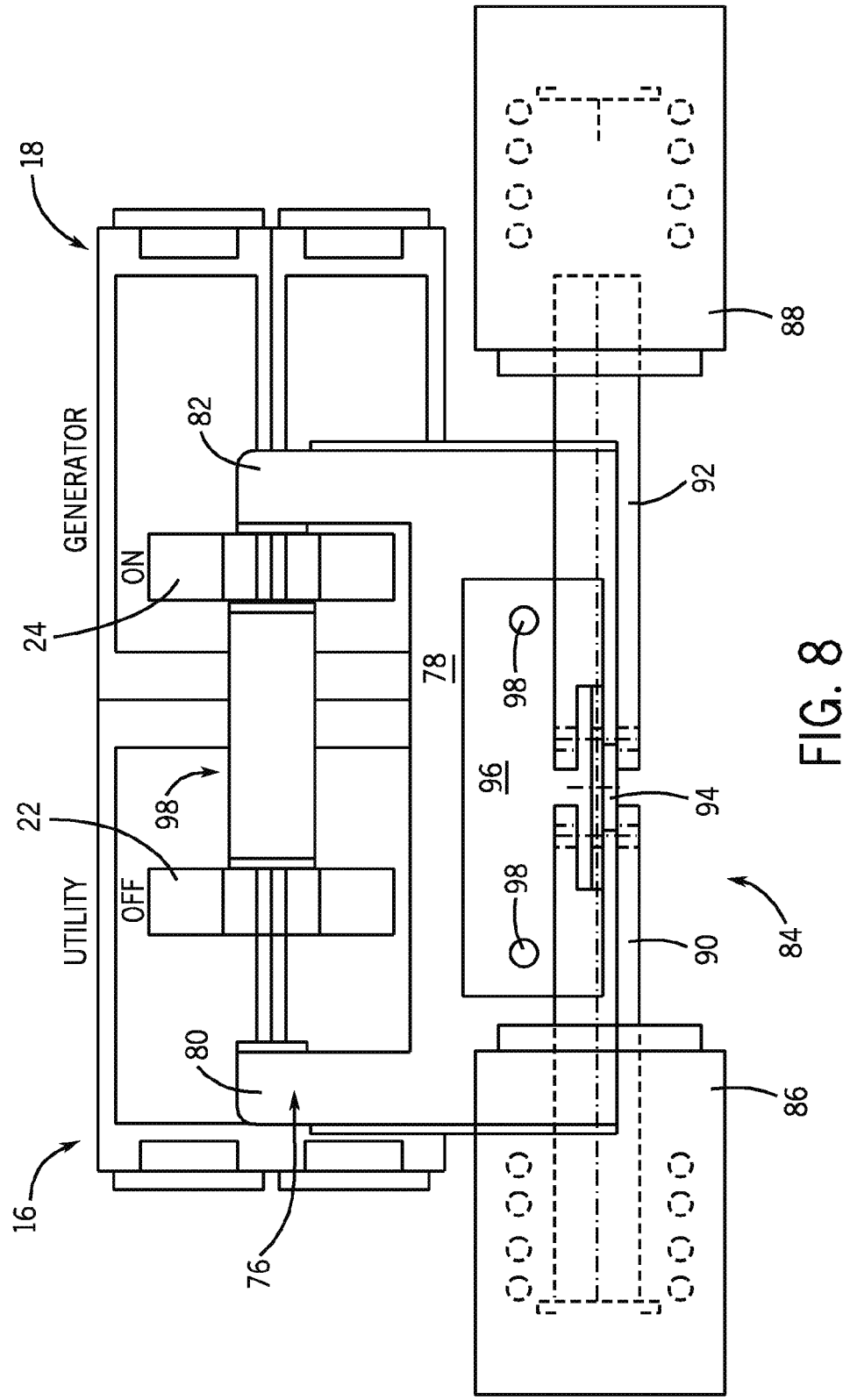
FIG. 8 is a front elevation view of the automatic transfer switch shown in FIG. 7 with the utility power supply switch in the OFF position and the backup generator power supply switch in the ON position.

An alternate embodiment of an automatic transfer switch having an interlock arrangement in accordance with the present invention is shown in FIGS. 7 and 8. In this embodiment, the pair of levers previously described are replaced with a shuttle 76 that is defined by a body 78 disposed between a pair of upright legs 80, 82. The shuttle 76 is translated linearly by a powered actuator, which may be in the form of an electromechanical actuator arrangement 84. More particularly, the shuttle 76 is translated along a linear axis so that a switch handle in the OFF position is pushed to the ON position by one of the upright legs.

The electromechanical actuator arrangement 84 may include a pair of solenoids 86, 88 each of which is capable of applying a pushing force. The solenoids 86, 88 are arranged so that their respective push forces oppose one another. Thus, the solenoids 86, 88 collectively provide reciprocating forces.

The armatures 90, 92 of the solenoids 86, 88, respectively, are pinned to a flange 94 of a solenoid bracket 96 to which the shuttle 76 is fastened by screws 98. The screws 98 extend through a slot (not shown) arranged linearly and defining a range of motion for the shuttle 76.

When utility power is energizing the electrical panel 10, switch handle 22 will be in the ON position and the switch handle 24 will be in the OFF position. The shuttle 76 will thus be positioned such that the upright leg 80 is generally adjacent the backside of switch handle 22 and the upright leg 82 is spaced from the switch handle 24, as shown in FIG. 7.

When utility power is interrupted, the generator will be started. After a defined period to allow the generator to reach steady-state operation, the solenoid 88 will be energized under power from the generator, thereby causing the shuttle 76 to be moved such that the upright leg 82 engages and pushes switch handle 24 from the OFF position to the ON position. An interlock arrangement 98 causes the switch handle 22 to first move to the OFF position before the switch handle 24 is switched to the ON position. This effectively switches the utility circuit breaker 16 OFF and then switches the generator circuit breaker 18 ON. In this "GENERATOR ON" position, the upright leg 80 of the shuttle 76 is spaced from the switch handle 22 and the upright leg 82 is adjacent the backside of switch handle 24. When the generator is started, power from the generator is used to power the solenoid 40.

When utility power is restored, the solenoid 86, which is powered by the utility power, will force the shuttle 76 back to its original position. More particularly, the solenoid 86 forces the shuttle 76 in the opposite direction, which results in the upright leg 80 pushing against the switch handle 22 and forcing the switch handle 22 to its ON position. However, before the switch handle 22 is moved to the ON position, the interlock member 98 causes the switch handle 24 to first be moved to its OFF position. As such, when utility power is restored, the electrical panel 10 is not electrically connected to both the utility power grid and the generator. Thereafter, the generator may be shut-down in a conventional manner.

Figure 9:
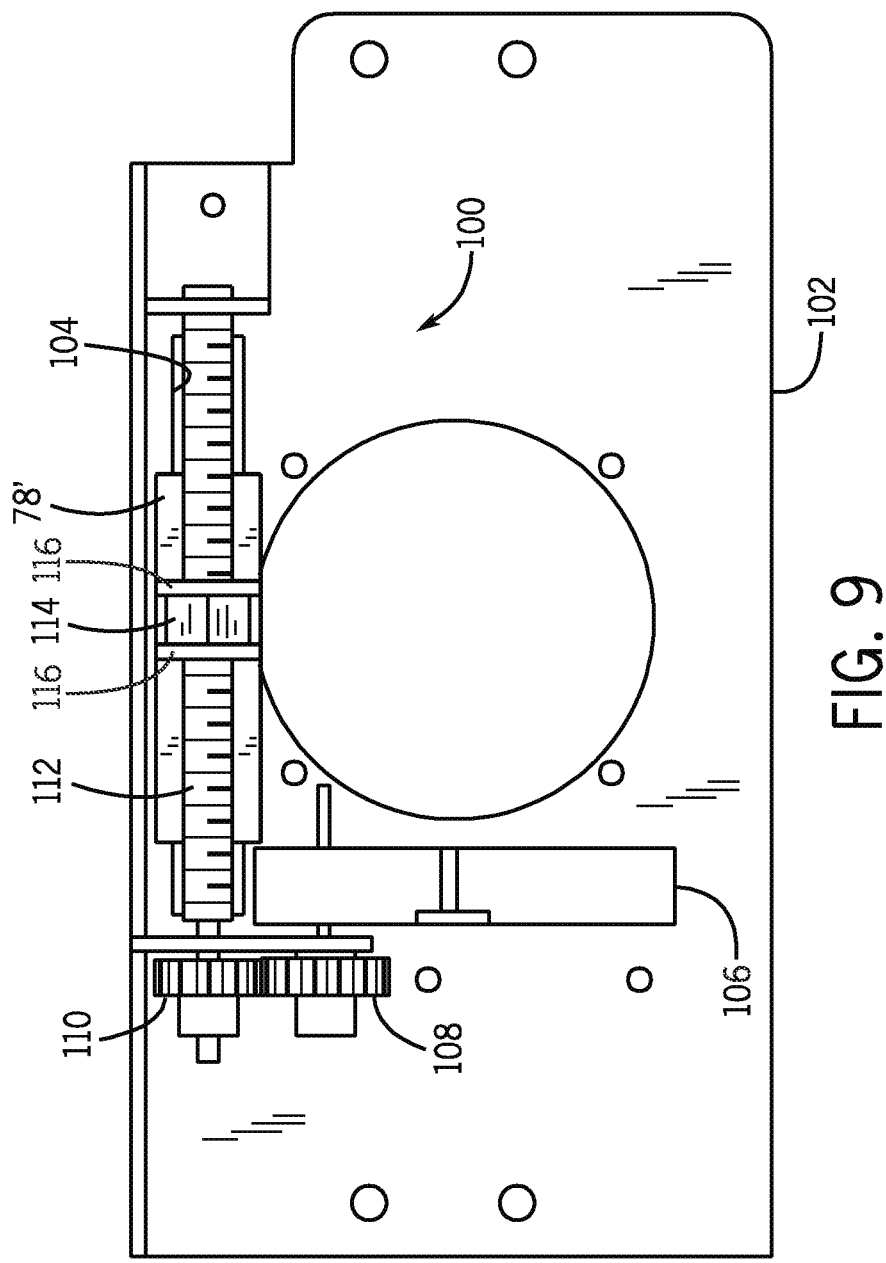
FIG. 9 is a rear elevation of an automatic transfer switch having a screw-type actuator arrangement according to another alternate embodiment of the invention.

In one embodiment, both of the solenoids 86, 88 are push-type solenoids. However, it is contemplated that both solenoids 86, 88 could be pull-type solenoids. Further, it is contemplated that a single push-pull type solenoid could be used. Additionally, it is recognized that other types of actuators could be used. For example, a screw actuator such as shown in FIG. 9 may be employed. In this embodiment, a screw actuator 100 may be employed to move the shuttle body, shown at 78', between positions. The screw actuator 100 is secured to a mounting plate 102 within which a slot 104 is formed, and shuttle body 78' extends through slot 104. A motor 106 is carried by the mounting plate 104, and rotates a drive gear 108 that is engaged with a driven gear 110, which in turn is secured to a drive screw 112. A nut 114 is engaged with the drive screw 112, and a pair of ears 116 are located one on either side of nut 114. With this arrangement, rotation of screw 112 by operation of motor 106 functions to move shuttle body 78' back and forth, to translate the shuttle 76. A rack and pinion arrangement could also be used to translate the shuttle 76. Similarly, other types of actuators could be used to translate carriages 52, 54 and thus cause pivoting of levers 30, 32. In addition, while the present invention has been shown in connection with power supply switches that are aligned, it is also understood that the present invention may be used in an arrangement in which the power supply switches are spaced apart from each other but not in alignment. In an embodiment such as this, the basic operation of the actuator and interlock arrangement is the same as shown and described herein, but accommodations are made to operate the switches, such as by altering the length of the levers.

It is appreciated that the control electronics for sensing the interruption and restoration of power may initiate various timed loops to ensure that the interruption or restoration of power is not temporary.

It will also be appreciated that the present invention may be used for any powered switching of interlinked switches and thus the invention is not limited to transfer panel or emergency panel applications.

The present invention has been described in terms of the preferred embodiment, and it is recognized that equivalents, alternatives, and modifications, aside from those expressly stated, are possible and within the scope of the impending claims.

I claim:

1. A method of switchably connecting distribution circuits of an electrical panel between first and second power sources, the electrical panel including first and second power supply switches, wherein the power supply switches include respective first and second switch operating members, the method comprising:
   detecting interruption of power from a power source providing power to the electrical panel; and
   energizing a rotatable powered actuator connected to the switch operating members of the power supply switches, wherein rotation of the powered actuator translates the switch operating members in a direction parallel to an axis of rotation of the powered actuator so as to apply a linear force to the first power supply switch operating member to move the first power supply switch operating member from a first position to a second position, and to also move the second power supply switch operating member from a second position to a first position by a control member slidably positioned between the first and second power supply switches, wherein when the first power supply switch operating member is in the second position and the second power supply switch operating member is in the first position, the distribution circuits are electrically connected to the second power source.

2. The method of claim 1 further comprising deenergizing the powered actuator after the first power supply switch operating member has been switched to the second position.

3. A transfer panel for electrically connecting a set of distribution circuits to an auxiliary power supply during interruption of primary power from a primary power supply, comprising:

a primary side switch having a primary side switch member switchable between an ON position and an OFF position, wherein the primary side switch member in the ON position connects the primary power supply to the set of distribution circuits;

an auxiliary side switch having an auxiliary side switch member switchable between an ON position and an OFF position, wherein the auxiliary side switch member in the ON position connects the auxiliary power supply to the set of distribution circuits;

a control member slidably positioned between the primary side switch member and the auxiliary side switch member that prevents both the primary side and secondary side switch members from being in the ON position at the same time; and a powered actuator arrangement that, upon operation of the powered actuator, applies a linear force that is parallel to an axis of operation of the powered actuator automatically to move the auxiliary side switch member to the ON position when the auxiliary power supply is ready to supply power, and wherein the control member causes the primary side switch member to automatically switch to the OFF position before the auxiliary side switch member reaches its ON position.

4. The transfer panel of claim 3 wherein the powered actuator arrangement includes a lever, a carriage, and an auxiliary side solenoid, and wherein the auxiliary side solenoid is automatically energized when the auxiliary power supply is energized during primary power supply failure, and wherein the solenoid has an armature connected to apply a pulling force to the carriage which in turn causes the lever to push the auxiliary side switch member from the OFF position to the ON position, and wherein the control member first causes the primary side switch member to move from the ON position to the OFF position.

5. The transfer panel of claim 3 wherein the powered actuator arrangement comprises a linearly translating shuttle that acts on the primary side and secondary side switch members to cause movement of the primary side and secondary side switch members between the respective ON and OFF positions.

6. The transfer panel of claim 5, wherein the powered actuator arrangement further comprises a rotatable screw-type actuator arrangement driven by a motor and engaged with the shuttle, wherein rotation of the screw-type actuator arrangement by the motor is operable to move the shuttle longitudinally along the screw-type actuator.

7. A transfer panel for electrically connecting a set of distribution circuits to an auxiliary power supply during interruption of primary power from a primary power supply, comprising:

a primary side switch having a primary side switch member switchable between an ON position and an OFF position, wherein the primary side switch member in the ON position connects the primary power supply to the set of distribution circuits;

an auxiliary side switch having an auxiliary side switch member switchable between an ON position and an OFF position, wherein the auxiliary side switch member in the ON position connects the auxiliary power supply to the set of distribution circuits;

a control member slidably positioned between the primary side switch member and the auxiliary side switch member that prevents both the primary side and secondary side switch members from being in the ON position at the same time; and a powered actuator arrangement that applies a linear force automatically to move the auxiliary side switch member to the ON position when the auxiliary power supply is ready to supply power, and wherein the control member causes the primary side switch member to automatically switch to the OFF position before the auxiliary side switch member reaches its ON position, wherein the powered actuator arrangement comprises a movable shuttle that acts on the primary side and secondary side switch members to cause movement of the primary side and secondary side switch members between the respective ON and OFF positions, and further comprises first and second opposed solenoids interconnected with the shuttle, wherein each solenoid is configured to transfer a linear actuating force through the shuttle to one of the primary side and secondary side switch members.

\* \* \* \* \*